United States Patent [19]

Cavan

[11] Patent Number: 4,811,409
[45] Date of Patent: Mar. 7, 1989

[54] METHOD AND APPARATUS FOR DETECTING DEFECT INFORMATION IN A HOLOGRAPHIC IMAGE PATTERN

[75] Inventor: Daniel L. Cavan, San Jose, Calif.

[73] Assignee: Insystems, Inc., San Jose, Calif.

[21] Appl. No.: 838,319

[22] Filed: Mar. 10, 1986

[30] Foreign Application Priority Data

Sep. 12, 1985 [JP] Japan .............................. 60-200687
Sep. 12, 1985 [KR] Rep. of Korea ..................... 85-6661

[51] Int. Cl.$^4$ .......................................... G06K 9/00
[52] U.S. Cl. .......................................... 382/8; 382/1; 382/65; 358/101; 358/106; 356/373; 356/375
[58] Field of Search ..................... 382/1, 8, 18, 31, 51, 382/63, 65, 67, 68; 358/101, 106, 107, 209, 212, 213; 356/373, 375, 379, 380, 386, 387, 399, 400; 250/204, 234, 235, 578; 350/162.12, 162.14

[56] References Cited

U.S. PATENT DOCUMENTS

| | | | |
|---|---|---|---|
| 3,900,737 | 8/1975 | Collier et al. | 250/492 A |
| 4,000,949 | 1/1977 | Watkins | 350/162.14 |
| 4,282,510 | 8/1981 | Southgate | 382/31 |
| 4,330,775 | 5/1982 | Iwamoto et al. | 382/31 |
| 4,516,833 | 5/1985 | Fusek | 350/162.12 |
| 4,578,810 | 3/1986 | MacFarlane et al. | 358/106 |
| 4,633,504 | 12/1986 | Wihl | 358/106 |
| 4,635,289 | 1/1987 | Doyle et al. | 382/8 |
| 4,707,734 | 11/1987 | Labinger et al. | 358/106 |

*Primary Examiner*—Leo H. Boudreau
*Assistant Examiner*—Jose L. Couso
*Attorney, Agent, or Firm*—Stoel Rives Boley Jones & Grey

[57] ABSTRACT

A method and an apparatus detect in a light pattern the presence of defects (10') in a photomask (10) to which the light pattern corresponds. An inspection area (36) that includes the light pattern is partitioned into stripe regions (72). The width (70) of a stripe region corresponds to the maximum extent of the image window (54) of a charge-coupled camera device (42) that is employed to scan continuously each stripe region at a nominally constant speed. Each stripe region is divided into a first array (90) of pixel elements (92) arranged in rows (94) and columns (96). The camera device comprises plural light detecting elements (84) that are arranged in a second array (82) of rows (86) and columns (88). The camera continuously traverses the columns of the first array in a direction along the length of the stripe region and acquires in row-by-row fashion quantities of charge which correspond to the intensities of the light present in the pixel elements with which the light detecting elements are aligned. The charge quantity measured for each pixel element in a row is shifted serially along a corresponding column of the second array in synchronism with, but in a direction opposite to, the motion of the camera device. The total charge quantity for each pixel element appears in the last row of light detecting elements. Each total charge quantity is converted to digital form by an analog-to-digital converter (222) and is then transferred to a threshold detector (224) which determines whether the quantity of light indicates the presence of a defect in the photomask.

15 Claims, 5 Drawing Sheets

METHOD AND APPARATUS FOR DETECTING DEFECT INFORMATION IN A HOLOGRAPHIC IMAGE PATTERN

BACKGROUND OF THE INVENTION

This invention relates to the inspection for defects arising during the fabrication of integrated circuits and, in particular, a method and an apparatus for scanning a light pattern to detect the presence of defects in a specimen subject to which the light pattern corresponds.

The use of light images in association with spatial filters has been suggested heretofore for determining the presence of defects in a photomask used in the fabrication of microminiature integrated circuits. One system that purports to accomplish this task is described in U.S. Pat. No. 4,000,949 of Watkins.

Light image constructed from holograms incorporated in optical processing apparatus are especially beneficial in that reverse ray tracing techniques can be employed during hologram reconstruction. Reverse ray tracing is advantageous in eliminating aberrations which are introduced by the optical components in the apparatus and which would spread out the light rays representing defects in a photomask pattern that was exposed to form the hologram. The spreading of light rays impairs the ability to detect the defects. A system employing reverse ray tracing techniques is described in U.S. Pat. No. 4,516,833 of Fusek.

The detection of defect image information in the light pattern can be accomplished in accordance with the following procedure. A light sensitive device having a defined imaging field is positioned to expose the device to and measure the intensity of light present in the defect image region of the size and shape of the imaging field and then is moved to the next adjacent region to repeat the measurement process. The problem with a detection procedure of this type is that relatively long settling times are required after movement of the light sensitive device from one measurement position to the next adjacent one. The reason is that the alignment position of the light sensitive device relative to the defect image region must be stable to ensure that detection of an image defect of submicron dimensions can be effected. A detection system of this type is, therefore, unacceptable in applications requiring relatively high throughput defect detection rates (i.e., the rate at which an array type photomask with normally identical elements can be inspected completely).

SUMMARY OF THE INVENTION

An object of this invention is to provide a method and an apparatus for detecting in a light pattern the presence of defects in a specimen subject to which the light pattern corresponds.

Another object of this invention is to provide such an apparatus that continuously scans the light image pattern to detect at high throughput rates defects of submicron dimensions in the specimen subject.

A further object of this invention is to provide in such an apparatus a mechanism that coordinates the scan and exposure operation to shorten the total time required to inspect the light pattern for defects in the specimen subject.

Yet another object of this invention is to provide such a method that promotes the detection of defect information of relatively low light intensity during continuous scanning of the light image.

The method and apparatus of the present invention are described by way of example with reference to a holographic imaging system that is useful for inspecting photomasks and detecting defects in them. The imaging system develops a defect image field whose dimensions and profile correspond to the physical layout of the photomask under inspection. An inspection area of the image field is partitioned into stripe regions of which each is approximately 0.65 millimeters in width. The width of a stripe region corresponds to the maximum extent of the image or optical window of a light detecting means or camera that is employed to scan each stripe region. The camera is a charge-coupled device that is mounted to an X-Y positioning table, which moves the camera along the strip region in a raster scan format. Control circuitry for the X-Y positioning table keeps the camera moving at a nominally constant speed as it traverses each strip region.

The determination of the presence of defects in the photomask is accomplished by detecting the presence of regions of light in each stripe region, which is divided into a first array of pixel elements. The charge-coupled camera device comprises plural light detecting elements that are arranged in a second array of 256 rows and 403 columns. In a preferred embodiment of the invention, each light detecting element has a rectangular aperture of 16 microns $\times$ 20 microns. The size of the second array dictates the size of the first array of pixel elements of which each pixel element has dimensions in proportion to those of a light detecting element. The number of columns of light detecting elements equals the number of columns of pixel elements and dictates the width of a stripe region. A lens that provides a tenfold magnification of the defect image field equalizes the dimensions of the pixel elements and the light detecting elements.

During a scan interval, the charge-coupled device continuously traverses the columns of the first array in a direction along the length of the strip region and acquires in row-by-row fashion measured energy values which correspond to the intensities of light present in the pixel elements with which the light detecting elements are aligned. In a preferred embodiment, a quantity of charge which is developed in a light detecting element of the charge-coupled device represents the measured energy value. The energy value is proportional to the product of the quantity of charge developed by the light intensity and the exposure time of the light detecting element.

The quantity of charge measured for each pixel element in a row is shifted serially along the corresponding column in synchronism with but in a direction opposite to the motion of the camera device along the stripe region. Each one of the light detecting elements in the last row of the second array has a total charge value which is nominally equal to 256 times that of the pixel element to which it is aligned. Since the light detecting elements do not have matched electrical characteristics, the quantity of charge developed in response to the light present in a given pixel element differs for different light detecting elements. The total charge value in each light detecting element in the last row of the second array represents, therefore, an average total charge for the corresponding pixel element.

The total of the 256 energy values accumulated for each pixel element in the last row of light detecting elements is converted by way of a video amplifier and an analog-to-digital converter to digital format and is transferred to a threshold detector which determines whether the quantity of light indicates the presence of a defect in the photomask. Whenever the charge-coupled device travels a distance of one row width along the stripe region, 403 total charge values are processed by the threshold detector. Whenever the threshold detector detects the presence of a defect, the position coordinates of the X-Y positioning table, together with information identifying the column of the pixel element and the total charge value in digital form, are stored in a large digital memory unit.

After the camera completes a scan of the stripe region, the stage retraces back to a different start location to begin a scan of the next adjacent stripe region. Overscan borders at both the start and stop locations for each stripe region provide regions for acceleration and deceleration of the X-Y positioning table and thereby enable a continuous scan at a nominally constant speed throughout the stripe region. This process is repeated until the entire inspection area of the defect light image field has been scanned.

The continuous scan of the defect image field by the charge-coupled device camera during energy value acquisition promotes photomask inspection at rapid throughput rates. The accumulation of only above-threshold information in the defect image field, in combination with the continuous scan capability, affords the rapid detection of defects of submicron dimensions that are represented by regions of light of relatively low intensity.

Additional objects and advantages of the present invention will be apparent from the following detailed description of a preferred embodiment thereof, which proceeds with refernce to the accompanying drawings.

DETAILED DESCRIPTION OF PREFERRED EMBODIMENT

Figure 1:
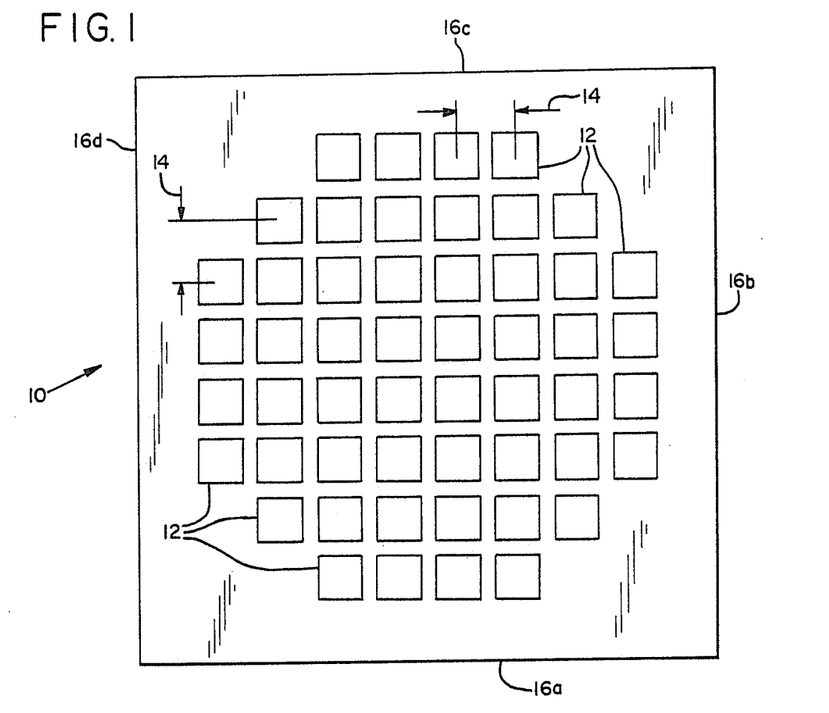
FIG. 1 is a diagram of an array type photomask from which a light image field of defect information is derived for inspection in accordance with the present invention.

FIG. 1 is a diagram of a photomask 10 which comprises a transparency, such as a chrome coated glass plate, that includes a planar array of normally identical photographic image elements 12 mutually spaced apart by a distance 14. Each image element 12 defines a circuit pattern which corresponds to a layer of an integrated circuit device that is fabricated in part with the use of the photomask. Photomask 10 is of rectangular shape with sides 16a, 16b, 16c, and 16d. The number of image elements 12 varies typically from between 20 and 500, although fewer or greater numbers are found in special instances. A noteworthy type of photomask which is called a reticle has only one image element.

Figure 2A:
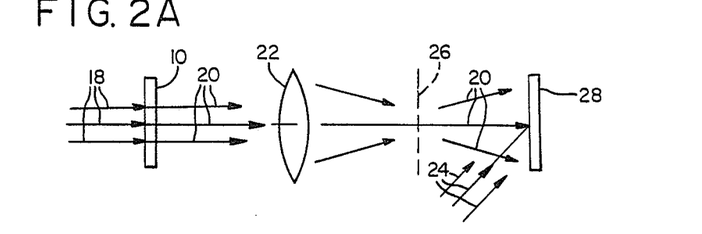
FIGS. 2A and 2B are diagrams of an optical processing system for, respectively, constructing a hologram of a photomask pattern and reconstructing from the hologram a defect light image corresponding to the photomask.
Figure 2B:
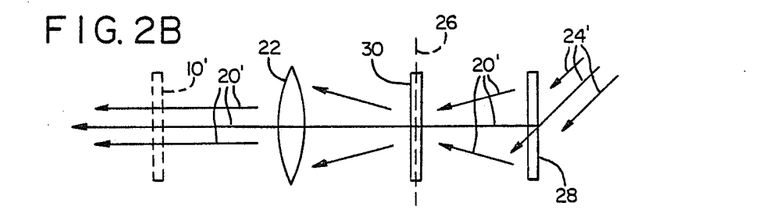

FIGS. 2A and 2B show optical processing apparatus for, respectively, constructing a hologram of photomask 10 and developing from the hologram a defect image corresponding to the photomask. The optical processing practiced with the use of such apparatus for inspecting photomasks for defects is described in the Fusek patent.

With reference to FIG. 2A, a subject beam 18 illuminates photomask 10 which diffracts the light rays incident to it. The diffracted light rays 20 pass through an imaging lens 22 and interfere with a reference beam 24 at a location beyond the Fourier transform plane 26 in the back focal plane of the imaging lens. The light rays 20 and the reference beam 24 interfere in a photographic recording medium to form a hologram 28. The hologram 28 records light information relating to the pattern of photomask 10 and the defects present in it.

With reference to FIG. 2B, a three-dimensional image 10' of photomask 10 is reconstructed from hologram 28 in the same optical processing system, which also includes a spatial filter 30 that conforms to the Fourier transform of an error-free photomask reference pattern. Spatial filter 30 is positioned in Fourier transform plane 26. Hologram 28 is illuminated by a light beam 24' that is coherent to but propagates in the conjugate direction of reference beam 24. Spatial filter 30 eliminates the light information corresponding to the photomask pattern from the reconstructed holographic light pattern. The light information or rays 20' not blocked by spatial filter 30 are reimaged by imaging lens 22 and represent the defects present in the photomask pattern. The holographic image 10' constitutes regions of relatively low intensity light. The holographic image 10' can describe photomask defects of submicron dimensions of about 0.5 micron. The light regions in defect image 10' appear in the same relative positions as the corresponding defects appear on photomask 10.

Figure 3:
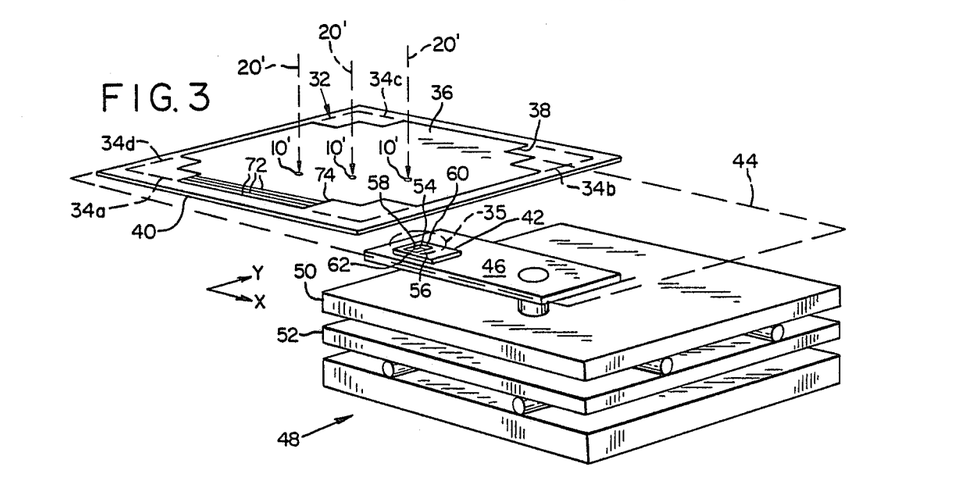
FIG. 3 is an isometric view of the scanning mechanism for detecting in a holographic light image field the presence of defects in the photomask of FIG. 1.

FIG. 3 is a diagram of a scanning mechanism for detecting in a holographic defect image 10' the presence of defects in photomask 10 to which the image corresponds. A defect image field 32 represents the region in the optical processing system in which statonary aerial light images 10' of relatively low intensity appear. Defect image field 32 is defined by sides 34a, 34b, 34c, and 34c, which correspond to the respective sides 16a, 16b, 16c, and 16d of, but do not necessarily have the same absolute dimensions as, photomask 10. In the preferred embodiment, a lens 35, which is shown in phantom, provides a tenfold magnification of the defect images 10' present in defect image field 32 relative to the size of photomask 10 for reaosns that will be described below.

The presence of defects in photomask 10 is determined by detecting within an inspection area 36 of defect image field 32 regions of light of intensities that exceed a predetermined threshold amount. Inspection area 36 includes the space contained within the outline 38, which is defined by the next adjacent sides of image elements 12 to the sides of photomask 10 in FIG. 1.

A defect image 10' that appears within image field 32 is formed by light rays 20' that converge in a horizontal plane 40. Lens 35 produces beneath plane 40 a defect image of tenfold magnification of that appearing in plane 40. The detection of defects is accomplished by scanning inspection area 36 in a raster type format with a light detecting means or camera 42 to sense the presence of light. The scanning procedure takes place within a plane 44 which is parallel to and beneath plane 40 and lens 35. In a preferred embodiment, camera 42 is solid state imaging device that comprises a charge-coupled device. One device of this type is a model SID504 chargecoupled device manfactured by RCA, New Products Division, Lancaster, PA 17604-3140, USA. The reference made herein to the design and architecture of the SID504 device are for purposes of illustration only.

Camera 42 and lens 35 are supported on a plate 46 that comprises a portion of an X-Y positioning table 48 which is cable of positioning camera 42 in plane 44 for alignment with any location in defect image field 32. A top of Y-stage 50 of positioning table 48 supports plate 46 and moves camera 42 along the Y direction in plane 44. A bottom or X-stage 52 of positioning table 48 moves camera 42 along the X direction in plane 44. One suitable type of X-Y positioning table is a model 8500 manufactured by Kensington Laboratories, Inc. of Richmond, Calif.

Figures 4A, 4B, 5:
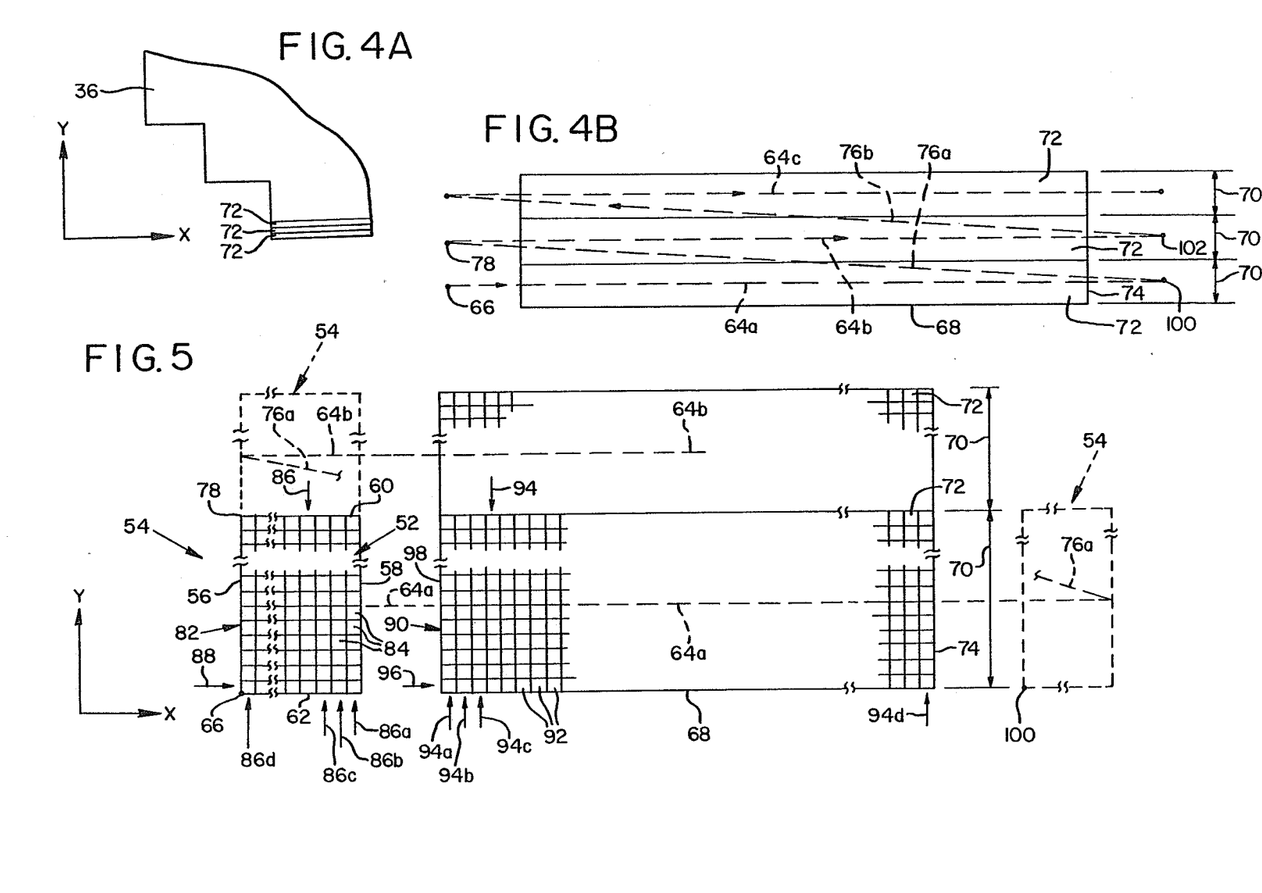
FIG. 4A is an enlarged fragmentry view showing three strip regions in the lower left-hand corner of the light image field of FIG. 3.
FIG. 4B is an enlarged, not to scale view of the stripe regions of FIGS. 3 and 4A that shows the raster scan path followed by a light detecting means to detect defect images in the light image field in accordance with the present invention.
FIG. 5 is a diagram showing the first array of pixel elements in the light image field under tenfold magnification and the second array of light detecting elements in the charge-coupled camera device used in the present invention.

FIGS. 4A and 4B are diagrams of, respectively, the outline of the lower left-hand corner of inspection area 36 in FIG. 3 and an enlarged portion thereof to show the raster scan path of camera 42. FIG. 5, which is an enlarged diagram of the portions of the stripe regions of FIG. 4B, shows the one-to-one correspondence between the dimensions of the light detecting elements of the second array and the pixel elements of the first array resulting from the tenfold magnification by lens 35.

With reference to FIGS. 3, 4A, 4B, and 5, camera 42 has an otpical window 54 through which light passes to be detected by it. Optical window 54 is a rectangle which has sides 56 and 58 that define its length and sides 60 and 62 that define its width.

In a normal scan operation, positioning table 48 moves camera 42 along a scan path segment 64a in the X direction from a start location 66 so that side 62 of optical window 54 is aligned with the segment 68 of inspection area 36. Sides 56 and 58 of optical window 54 are parallel to the Y direction and define the width 70 of a stripe region 72 (three of which are shown in FIG. 3) which represents the portion of inspection area 36 traversed by camera 42 as it moves in the X direction.

After side 56 of optical window 54 moves past segment 74 of inspection area 36, positioning table 48 moves camera 42 along a retrace path segment 76a to a start location 78 to scan a second adjacent stripe region 72. During retrace, Y-stage 50 moves camera 42 at a distance equal to width 70 of strip region 72, and X-stage 52 moves camera 42 a distance equal to the length of path segment 64a. After retrace, positioning table 48 moves camera 42 along path segment 64b in the X direction from start location 78 to traverse a second strip region 72 of width 70.

The above-described scanning and retrace procedure is repeated until the entire inspection area 36 is traversed by camera 42. There are, however, differences in the lengths of the scan and retrace path segments to accommodate the difference in the dimensions in the X direction of inspection area 36.

With particular reference to FIG. 5, camera 42 of the preferred embodiment is an RCA model SID504 charge-coupled device that includes an array 82 of light detecting elemetns 84 arranged in rows 86 and columns 88. Array 82 has 256 rows and 403 columns of light detecting elements 84. A row 86 is defined as a group of elements 84 arranged in a line perpendicular to the scan direction (i.e., in the Y direction), and a column 88 is defined as a group of elements 84 arranged in a line parallel to the scan direction (i.e., in the X direction). Each row 86 and each column 88 have lengths of 6.5 millimeters and 4.9 millimeters, respectively. Each light detecting element 84 is 20 microns in length and 16 microns in width. The width of each one of stripe regions 72 is, therefore, equal to the total distance spanned by a row of 403 light detecting elements. Each one of light detecting elements 84 receives through optical window 54 light rays that emanate from the portion of inspection area 36 with which it is aligned and stores in its potential well a quantity of charge or measured energy value that corresponds to the intensity of the light rays incident to it.

Each stripe region 72 of inspection area 36 is divided into an array 90 of pixel elements 92, of which each has the same dimensions as light detecting elements 84 of array 82 by the operation of lens 35. Pixel elements 94 of array 90 are arranged in rows 94 and columns 96, each row having 403 pixel elements and each column having a number of pixel elements dictated by the length of the stripe region 72. The presence of light in the stripe regions is detected by moving optical window 54 of camera 42 along each one of stripe regions 72 and acquiring the energy value corresponding to the intensity of light in each one of pixel elements 92 in accordance with the following procedure.

X-stage 52 commences the scanning process by accelerating optical window 54 from start location 66 toward the right in the X direction until its side 58 is collinear with segment 98 of inspection area 36. X-stage 52 then moves optical window 54 at a nominally constant predetermined speed along stripe region 72.

Whenever light detecting elements 84 in the first row 86a of array 82 align with pixel elements 92 in the first row 94a of array 90, the following events take place. An electrical charge develops in the potential well of each one of light detecting elements 84 in row 86a. The quantity of charge corresponds to the intensity of light present in the pixel element. (The potential wells of light detecting elements 84 have no charge accumulated in them prior to the scan of a stripe region 72.) A ROW TRANSFER clock signal that is applied to each row 86 of array 82 transfers the charge from each light detecting element 84 in row 86a to the light detecting element in the same column 88 but in the next adjacent or second row 86b. This transfer takes place about the time the light detecting elements and the pixel elements are aligned with each other. (Since X-stage 52 continuously moves optical window 54 along stripe region 72, there is a negligible amount of image degradation that results from aliasing between adjacent rows of the pixel elements.) After the transfer of charge from row 86a to row 86b, there exists no accumulated charge in the potential wells of light detecting elements 84 in row 86a.

Whenever light detecting elements 84 in second row 86b align with pixel elements 92 in the second row 94b of array 90, the following events take place. An electrical charge develops in the potential well of each light detecting element 84 in rows 86a and 86b. The quantity of charge developed in each one of the light detecting elements 84 in row 86b is added to the charge previously tranferred to it. The quantity of charge in the light detecting elements 84 in row 86b represents, therefore, two energy values corresponding to the intensity of light present in a pixel element 92 in each column of row 94a of array 90. The ROW TRANSFER clock signal transfers the charge from each light detecting element 84 in row 86b and row 86a to the light detecting element in the same column 88 but in the next adjacent third row 86c and second row 86b, respectively.

The above-described procedure of (1) acquiring in a light detecting element 84 in a row 86 an energy value corresponding to the intensity of light in a pixel element 94 with which the light detecting element is aligned and (2) transferring the energy value to the light detecting element 84 in the same column 88 but in the next adjacent row 86 with which the pixel element 92 has not previously been aligned is repeated for 255 cycles of the ROW TRANSFER clock signal.

Whenever 255 such row-to-row transfers have been completed, the light detecting elements in the 256th or last row 86d of array 82 align with the pixel elements 92 in first row 94a of array 90. The 255 previously accumulated energy values for each pixel element 92 in first row 94a are added to the 256th energy value acquired by each light detecting element 84 in last row 86d. Prior to the occurrence of the 256th ROW TRANSFER clock signal, energy values accumulated in the 403 light detecting elements 84 corresponding to the pixel elements 92 in row 94a are read out serially by a high-speed DATA TRANSFER clock signal. The accumulated energy values for pixel elements 94 are converted to a digital format and processed by a threshold detector to determine whether the amount of light present in each pixel element 92 indicates the presence of a defect in a corresponding location in photomask 10.

Upon the occurrence of the 256th cycle of the ROW TRANSFER block signal, the 255 previously accumulated energy values for each pixel element 94 in second row 94b are added to the 256th energy value acquired by each light detecting element 84 in last row 86d. Prior to the occurrence of the 257th cycle of the ROW TRANSFER clock signal, the contents of the 403 light detecting elements 84 corresponding to the pixel elements 92 in row 94b are read out and processed as described above.

For each succeeding cycle of the ROW TRANSFER clock signal, the scan of stripe region 72 continues such that 256 energy values for each pixel element 92 in a row 94 and a column 96 of array 90 are accumulated in the light detecting element 84 in the corresponding column 88 and row 86d of array 82.

There are several general aspects of the accumulation of energy values that characterize the scanning process of the present invention. First, each one of the light detecting elements 84 in row 86a never accumulates more than one energy value for any one of the pixel elements 92 with which it becomes aligned. Second, the light detecting elements 84 in a row 86 presently aligned with the pixel elements 92 in a particular row 94 always have one more energy value accumulated in them than the light detecting elements 84 in the next adjacent row 86 that was previously aligned with the particular row 94 of pixel elements 92. Third, each one of the light detecting elements 84 in row 86d accumulates 256 energy values corresponding to the light present in the pixel element 92 with which it is aligned.

After side 56 of optical window 54 travels past segment 74 of inspection area 36, the scan of a stripe region 72 is completed, and the accumulated energy values of the pixel elements 92 in the last row 94d of array 90 have been read out from the light detecting elements 84 of the last row 86d of array 82. X-stage 52 decelerates optical window 54 to a stop at stop location 100. (In FIG. 5, optical window 54 is shown in phantom in this position.) X-stage 52 and Y-stage 50 retrace camera 42 along path segment 76a to position optical window 54 at start location 78. The potential wells of light detecting elements 84 are cleared during this time in preparation for the scan of the next adjacent stripe region 72. The scan and retrace of the second and succeeding stripe regions 72 proceed as described above.

Figure 6:
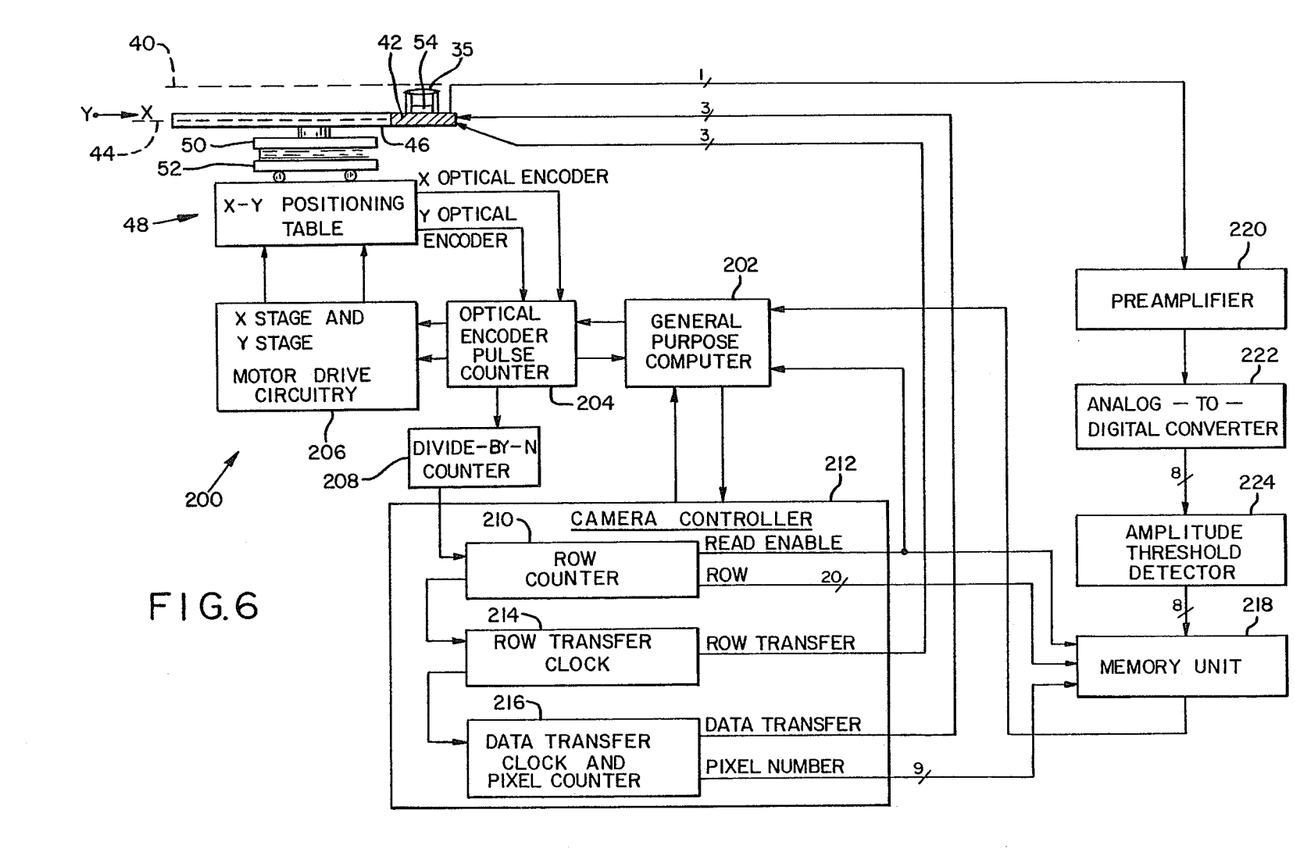
FIG. 6 is a block diagram of the apparatus for scanning the light image field for defects in the photomask of FIG. 1 in accordance with the present invention.
Figure 7:
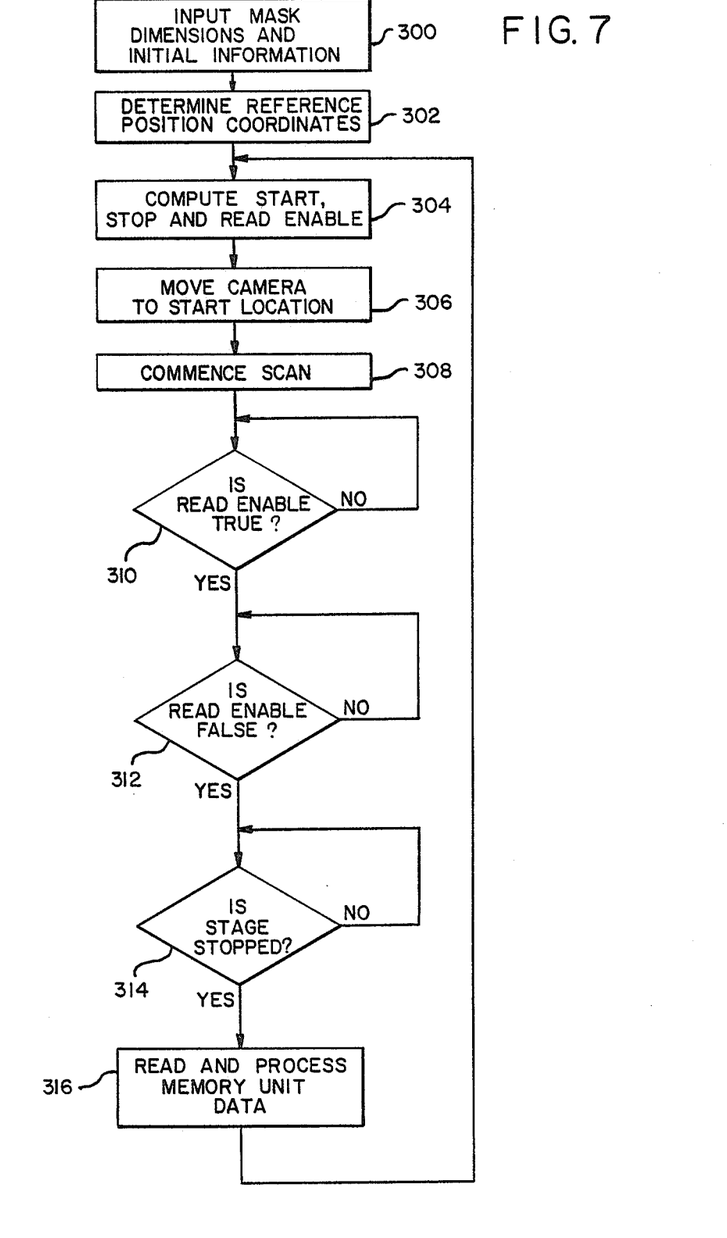
FIG. 7 is a flow diagram that shows the defect image processing carried out by a general purpose computer included in the apparatus of FIG. 6.

FIG. 6 is a block diagram of the apparatus for scanning a holographic defect image for defects in accordance with the present invention. FIG. 7 is a flow diagram showing the interrelationship of the various functions carried out by a general purpose computer included in the apparatus of FIG. 6. The description below of the operation of the scanning apparatus of FIG. 6 is presented with parenthetical references to the appropriate process or decision blocks in the flow diagram of FIG. 7.

With reference to FIGS. 6 and 7, the scanning apparatus 200 employs a general purpose computer 202 to control the motion of X-Y positioning table 48 and the acquisition and identification by row 94 and column 96 of the measured energy values corresponding to the intensities of light present in the pixel elements 92 of array 90. Prior to the commencement of a scanning procedure, certain initial information is inscribed in the memory of computer 202 (FIG. 7, process block 300). The initial information includes the profile and dimensions of inspection area 36 for a particular photomask 10, scan speed and acceleration and deceleration rates of X-stage 52, and width 70 of stripe regions 72. The X-Y positioning table 48 has a precision optical encoder for each of the X- and Y-stages. Each optical encoder develops an output pulse for each 0.4 micron of stage displacement. The exact instantaneous location of camera 42 is established by first visually aligning its side 58 with segment 98 of inspection area 36 and then recording the position coordinates of X-stage 52 and Y-stage 50 (FIG. 7, process block 302). This reference location is inscribed in the memory of computer 202, and the instantaneous position of camera 42 is monitored relative to it.

Computer 202 calculates from the photomask profile and reference location information stored in its memory the start location 66 and stop location 100 for camera 42 in preparation for the scan of the first stripe region 72 (FIG. 7, process block 304). Computer 202 also calculates relative to array 90 the locations of camera 42 between which a READ ENABLE signal appears. The READ ENABLE signal enables the storage in memory of the abovethreshold accumulated energy values, together with their stripe region, row, and column locations as will be described below (FIG. 7, process block 304).

Computer 202 develops a command that is delivered to an optical encoder pulse counter 204 which forms a part of a servomechanism for the drive motors for X-stage 52 and Y-stage 50. The drive motors are an integral part of positioning table 48. This command includes the number of 0.4 micron increments in both the X and Y directions for moving camera 42 to its start location 66. Optical encoder pulse counter 204 delivers control signals to the X-stage and Y-stage motor drive circuitry 206, which provides the drive signals to X-stage 52 and Y-stage 50 to move then to start location 66 (FIG. 7, process block 306). Optical encoder pulse counter 204 counts the pulses developed at the outputs of the X and Y optical encoders included in positioning table 48 and continues to apply the drive signals until the numbers of pulses counted correspond to the numbers of 0.4 micron increments delivered from computer 202. Optical encoder pulse counter 204 terminates the drive signals to motor drive circuitry 206 as soon as camera 42 reaches start location 66.

To begin the scan of the first stripe region 72, computer 202 delivers a command to optical encoder pulse counter 204 to accelerate the movement of X-stage 52, which achieves a nominally constant scan speed when its side 56 is collinear with segment 98 of inspection area 36. As X-stage 52 moves camera 42 from start location 66, optical encoder pulse counter 204 counts the pulses produced by the X and Y optical encoders and delivers the X optical encoder pulses to a divide-by-N counter 208, which provides at its output one pulse for every five pulses appearing at the output of the X optical encoder (i.e., N=5). A row counter 210, which comprises a part of a camera controller 212, receives and counts the pulses appearing at the output of divide-by-N counter 208. General purpose computer 202 provides to row counter 210 count information that corresponds to the beginning and ending positions of optical window 54 in the stripe region 72 at which it can send the acquired energy values to memory. As soon as it reaches the beginning count, row counter 210 develops a READ ENABLE command that enables the accumulated energy valuees to be stored in memory.

Each pulse appearing at the output of divide-by-N counter 208 corresponds to a 2 micron increment of optical window 54 during the scan of a stripe region 72. Since the image appearing in plane 40 and beneath lens 35 represents a tenfold magnification of the holographic image of photomask 10, the movement by optical window 54 of 2 microns in the X direction corresponds to a 20 micron increment in the X direction within plane 40. The 20 micron distance corresponds to the 20 micron length of a pixel element 92 or the width of a row. Each pulse that appears at the output of divide-by-N counter 208 represents, therefore, a displacement of optical window 54 by the length of one pixel element 92 or a row width in the X direction.

Row counter 210 counts, therefore, the number of rows 94 of array 90 traversed by camera 42. Camera controller 212 also includes a row transfer clock generator 214 and a data transfer clock generator and pixel counter 216. As optical window 54 of camera 52 traverses in plane 44 the defect image field 32 at a rate of 29 mm/sec, row counter 210 provides in response to each pulse that appears at the output of divide-by-N counter 208 a signal to row transfer clock generator 214 which develops the ROW TRANSFER clock signal of 1 MHz that provides one three-phase clock cycle to each row 86 of the light detecting elements 84. After the completion of each ROW TRANSFER clock cycle, data transfer clock generator and pixel counter 216 develops the DATA TRANSFER clock signal of 8 MHz that provides 403 three-phase clock cycles to row 86d of light detecting elements 84.

It will be appreciated that the production of the ROW TRANSFER and DATA TRANSFER clock signals is synchronized to the displacement of the X-stage 52 during the scan of a stripe region 72. Production of the ROW TRANSFER and DATA TRANSFER clock signals takes place, therefore, only after X-stage 52 travels a distance of 2 microns along plane 44, irrespective of the time required to do so. Such synchronism ensures that the alignment of a light detecting element 84 and a corresponding pixel element 92 is preserved whenever the scan speed of X-stage 52 changes from its nominal value by reason of, for example, externally generated vibrations. This feature is important in determining the exact location of defect information of submicron dimension in the light pattern.

During the first 255 cycles of the ROW TRANSFER clock signal, 255 pixel elements 92 in each of the 403 columns 96 of array 90 are scanned. The energy values of the 255 scanned pixel elements 92 in each column 96 of array 90 accumulate in the light detecting elements 84 of array 82 as described above. After the 255th cycle of the ROW TRANSFER clock signal, the 256 energy values accumulated for the first row 94a of pixel elements 92 appear in row 86d of array 82. Row counter 210 then develops the READ ENABLE signal, which enables a memory unit 218 to receive in digital format the accumulated energy values stored in the columns 88 of light detecting elements 84 for the row 94a of pixel elements 94 (FIG. 7, decision block 310). As stated above, row counter 210 receives from computer 202 the beginning and ending row pulse counts between which the READ ENABLE signal is to appear. Memory unit 218 has a storage capacity of 512 Kbytes.

The energy values read out of row 86d of light detecting elements 84 are conditioned and amplified by a preamplifier circuit 220 and converted to digital format by analog-to-digital converter 222. The energy value represented by each digital word is applied to and discriminated by a threshold detector 224. Only the digital words of the pixel elements 92 whose accumulated energy values exceed the predetermined threshold level of threshold detector 224 are stored in memory unit 218, and the remaining digital words are discarded. A pixel element 92 is identified in memory unit 218 by its position in a row 94 and a column 96 in array 90, the row being identified by the output of row counter 210 and the column being identified by the pixel number recorded in data transfer clock generator and pixel counter 216 as the series of energy values is read out of row 86d of array 82. Computer 202 inscribes in its internal memory a datum word identifying the stripe region from which the stored pixel elements were taken.

The data transfer clock generator and pixel counter 216 continues to provide 403 cycles of the DATA TRANSFER clock signal for each cycle of the ROW TRANSFER clock signal in excess of 255 until the accumulated energy values for all pixel elements 92 in a stripe region 72 are read out of row 86d of array 82. After side 56 of optical window 54 travels past segment 74 of inspection area 36, row counter 210 terminates the READ ENABLE signal, indicating that the energy values of pixel elements 92 in row 94d of array 90 have been read out of the light detecting elements 84 in row 86d of array 82 (FIG. 7, decision block 312). Upon the termination of the READ ENABLE signal, optical encoder pulse counter 204 decelerates the motion of camera 42 and stops it at stop location 100 (FIG. 7, decision block 314). The data collected in memory unit 218 for the first stripe region 72 are read into and processed by general computer 202 (FIG. 7, process block 316).

After camera 42 reaches stop location 100, computer 202 calculates the start location 78 and stop location 102 of the next adjacent or second stripe region 72 (FIG. 7, process block 304). Computer 202 initates the retrace of camera 42 along retrace path segment 76a to start location 78 and then commences the scan of the next adjacent stripe region 72 in a similar manner to that described above (FIG. 7, process blocks 306 and 308). The scanning of inspection area 36 continues until energy vaues have been collected for all of the pixel elements 92 in each of the stripe regions 72.

It will be obvious to those having skill in the art that many changes may be made in the above-described details of the preferred embodiment of the present invention. The scope of the present invention should be determined, therefore, only by the following claims.

What is claimed is:

1. A method of detecting in a light pattern the presence of defects in a specimen subject to which the light pattern corresponds, comprising:

providing a light detector to detect light from the light pattern, the light detector comprising light detecting elements arranged in a first array of rows and columns and defining in the light pattern plural adjacent stripe regions each of which includes plural pixel elements arranged in a second array of rows and columns, and each light detecting element being operable to provide a measured energy value corresponding to the amount of light present in any one of the pixel elements;

successively aligning each one of the light detecting elements in a column of the first array with a pixel element so that each one of the light detecting elements in the column acquires an energy value corresponding to the pixel element, thereby to acquire for the pixel element a number of energy values that equals the number of light detecting elements in the column;

accumulating the number of energy values to provide a total energy value corresponding to the amount of light present in the pixel element and proportional to the sum of the number of energy values; and determining from the total energy value whether the amount of light present in the pixel element represents a defect in the specimen subject.

2. The method of claim 1 in which the light pattern is stationary and the successive alignment of the light detecting elements in the column is accomplished by continuously moving the first array of light detecting elements along the light pattern stripe region in which the pixel element is located.

3. The method of claim 1 in which each one of the light detecting elements in the column comprises a part of a charge-coupled device and produces a quantity of charge which represents an energy value, and the number of energy values are accumulated to provide the total energy value by moving the light detecting elements in the column in a scan direction serially past the pixel element and shifting in a direction opposite the scan direction along the column the quantity of charge measured by the light detecting element in present alignment with the pixel element to the next adjacent light detecting element in the column.

4. Apparatus for detecting in a light pattern the presence of defects in a specimen subject to which the light pattern corresponds, comprising:

light detecting means for detecting light from the light pattern, the light detecting means comprising light detecting elements arranged in a first array of rows and columns and defining in the light pattern plural adjacent stripe regions each of which includes plural pixel elements arranged in a second array of rows and columns, and each light detecting element being operable to provide a measured energy value corresponding to the amount of light present in any one of the pixel elements;

scanning means to scan the light detecting means along a stripe region so that in succession each light detecting element in one column of the first array traverses and acquires an energy value corresponding to the amount of light present in a pixel element in one column of the second array;

accumulating means to accumulate a total energy value proprotional to the sum of the energy values acquired for the pixel element by all of the light detecting elements in the one column of the first array; and means to determine from the total energy value whether the amount of light in the pixel element represents a defect in the specimen subject.

5. The apparatus of claim 4 in which the light detecting means comprises a charge-coupled device.

6. The apparatus of claim 4 in which the light pattern remains stationary and the scanning means further comprises positioning means to position the light detecting means across each one of the stripe regions to scan them in a serial manner.

7. The apparatus of claim 6 in which the positioning means moves the light detecting means continuously across each stripe region.

8. The apparatus of claim 4 in which the first array has a first row and N total number of rows and which further comprises position-detecting means for detecting the position of the first array relative to the stripe region, the position-detecting means cooperating with the accumulating means so that each one of the lihgt detecting elements in the first row of the one column never accumulates more than one energy value for any one of the pixel elements of the second array with which it becomes aligned, and each one of the light detecting elements in the Nth row of the one column has accumulated N number of energy values for any one of the pixel elements with which it becomes aligned.

9. The apparatus of claim 4 in which the light pattern is derived from reconstruction of a hologram that corresponds to the specimen pattern.

10. The appartus of claim 4 in which the specimen pattern is that of a photomask.

11. Apparatus for detecting a light pattern of relatively low intensity, comprising:

light detecting means including a first array of light detecting elements arranged in rows and columns to detect light from the light pattern, the light detecting means defining in the light pattern plural adjacent stripe regions each of which includes plural pixel elements arranged in a second array of rows and columns, and each light detecting element comprising a part of a charge-coupled device and being operable to produce a quantity of charge corresponding to the amuont of light present in any one of the pixel elements;

scanning means to scan the light detecting means along a stripe region so that each light detecting element in one column of the first array traverses each pixel element in one column of the second array; and accumulating means to accumulate for each one of the pixel elements in the one column of the second array at total quantity of charge proportional to the sum of the quantities of charge acquired by all of the light detecting elements in the one column of the first array, the total quantity of charge being accumulated by moving the light detecting elements in the column in a scan direction serially past the pixel element and shifting in a direction opposite the scan direction along the column the quantity of charge measured by the light detecting element in present alignment with the pixel element to the next adjacent light detecting element in the column.

12. The apparatus of claim 11 in which the light pattern remains stationary and the scanning means further comprises positioning means to position the light detecting means across each one of the stripe regions to scan them in a serial manner.

13. The apparatus of claim 12 in which the scanning means moves the light detecting means continuously across each stripe region.

14. A method of detecting in a light pattern the presence of defects in a specimen subject to which the light pattern corresponds, comprising:
providing a light detector to detect light from the light pattern, the light detector comprising light detecting elements arranged in a first array of rows and columns and defining in the light pattern plural adjacent stripe regions each of which includes plural pixel elements arranged in a second array of rows and columns, and each one of the light detecting elements in a column comprising a part of a charge-coupled device and being operable to produce a quantity of charge which represents an energy value corresponding to the amount of light present in any one of the pixel elements;
successively aligning each one of the light detecting elements in a column of the first array with a pixel element to acquire a number of energy values that equals the number of light detecting elements in the column;
accumulating the number of energy values to provide a total energy value by moving the light detecting elements in the column in a scan direction serially past the pixel element and shifting in a direction opposite the scan direction along the column the quantity of charge measured by the light detecting element in present alignment with the pixel element to the next adjacent light detecting element in the column; and
determining from the total energy value whether the amount of light present in the pixel element represents a defect in the specimen subject.

15. Apparatus for detecting in a light pattern the presence of defects in a specimen subject to which the light pattern corresponds,. comprising:
light detecting means for detecting light from the light pattern, the light detecting means comprising light detecting elements arranged in a first array of rows and columns having a first row and N total number of rows and defining in the light pattern plural adjacent stripe regions each of which includes plural pixel elements arranged in a second array of rows and columns, and each light detecting element being operable to provide a measured energy value corresponding to the amount of light present in any one of the pixel elements;
scanning means to scan the light detecting means along a stripe region so that each light detecting element in one column of the first array traverses each pixel element in one column of the second array;
accumulating means to accumulate for each one of the pixel elements in the one column of the second array a total energy value proportional to the sum of the energy values acquired by all of the light detectign elements in the one column of the first array;
position-detecting means for detecting the position of the first array relative to the stripe region, the position-detecting means cooperating with the accumulating means so that each one of the light detecting elements in the first row of the one column never accumulates more than one energy value for any one of the pixel elements of the second array with which it becomes aligned, and each one of the light detecting elements in the Nth row of the one column has accumulated N number of energy values for any one of the pixel elements with which it becomes aligned; and
means to determine from the total energy value for any one pixel element in the one column whether the amount of light in the one pixel element represents a defect in the specimen subject.

* * * * *

UNITED STATES PATENT AND TRADEMARK OFFICE
CERTIFICATE OF CORRECTION

PATENT NO. : 4,811,409

DATED : March 7, 1989

INVENTOR(S) : Daniel L. Cavan

It is certified that error appears in the above-identified patent and that said Letters Patent is hereby corrected as shown below:

Column 1, line 19, change "image" to --images--.

Column 1, line 64, change "operation" to --operations--.

Column 2, line 17, change "strip" to --stripe--.

Column 2, line 20, change "strip" to --stripe--.

Column 2, line 40, change "strip" to --stripe--.

Column 3, line 35, change "refernce" to --reference--.

Column 3, line 50, change "fragmentry" to --fragmentary--.

Column 3, line 51, change "strip" to --stripe--.

Column 4, line 59, change "statonary" to --stationary--.

Column 4, line 62, change "34c" to --34d--.

Column 4, line 68, change "reaosns" to --reasons--.

Column 5, line 17, after "is" insert --a--.

Column 5, line 20, change "chargecoupled device manfactured" to --charge-coupled device manufactured--.

Column 5, line 22, change "reference" to --references--.

Column 5, line 29, change "of" (first occurrence) to --or--.

Column 5, line 46, change "otpical" to --optical--.

UNITED STATES PATENT AND TRADEMARK OFFICE
CERTIFICATE OF CORRECTION

PATENT NO. : 4,811,409

DATED : March 7, 1989

INVENTOR(S) : Daniel L. Cavan

It is certified that error appears in the above-identified patent and that said Letters Patent is hereby corrected as shown below:

Column 5, line 65, change "strip" to --stripe--.

Column 6, line 1, change "strip" to --stripe--.

Column 6, line 12, change "elemetns" to --elements--.

Column 6, line 34, change "94" to --92--.

Column 6, line 36, change "403" to --403--.

Column 7, line 30, change "255" to --255--.

Column 7, line 38, change "403" to --403--.

Column 7, line 42, change "94" to --92--.

Column 7, line 48, change "block" to --clock--.

Column 7, line 49, change "94" to --92--.

Column 7, line 53, change "403" to --403--.

Column 8, line 67, change "abovethreshold" to --above-threshold--.

Column 10, line 6, change "403" to --403--.

Column 10, line 22, change "dimension" to --dimensions--.

Column 10, line 24, change "403" to --403--.

Column 10, line 29, change "256" to --256--.

UNITED STATES PATENT AND TRADEMARK OFFICE
CERTIFICATE OF CORRECTION

PATENT NO. : 4,811,409              Sheet 3 of 3
DATED      : March 7, 1989
INVENTOR(S): Daniel L. Cavan It is certified that error appears in the above-identified patent and that said Letters Patent is hereby corrected as shown below:

Column 10, line 36, change "94" to --92--.

Claim 8, column 12, line 49, change "lihgt" to --light--.

Claim 11, column 13, line 5, change "amuont" to --amount--.

Claim 15, column 14, line 15, change "corresponds,." to --corresponds,--.

Claim 15, column 14, line 36, change "detectign" to --detecting--.

Signed and Sealed this

Twentieth Day of February, 1990

*Attest:*

JEFFREY M. SAMUELS

*Attesting Officer*  *Acting Commissioner of Patents and Trademarks*